United States Patent
Takebayashi (10) Patent No.: US 8,246,352 B2
(45) Date of Patent: Aug. 21, 2012

(54) SURGICAL GUIDE AND A METHOD FOR POSITIONING A DRILL USING THE SURGICAL GUIDE

(76) Inventor: Akira Takebayashi, Saitama (JP)

( * ) Notice: Subject to any disclaimer, the term of this patent is extended or adjusted under 35 U.S.C. 154(b) by 0 days.

(21) Appl. No.: 12/918,516

(22) PCT Filed: Feb. 26, 2009

(86) PCT No.: PCT/JP2009/053564
§ 371 (c)(1),
(2), (4) Date: Aug. 20, 2010

(87) PCT Pub. No.: WO2009/107723
PCT Pub. Date: Sep. 3, 2009

(65) Prior Publication Data
US 2010/0323320 A1    Dec. 23, 2010

(30) Foreign Application Priority Data

Feb. 28, 2008  (JP) ................. 2008-048114

(51) Int. Cl.
*A61C 3/00*  (2006.01)
*A61C 1/00*  (2006.01)
(52) U.S. Cl. ........................... 433/75; 433/29
(58) Field of Classification Search ............. 433/72–75, 433/215, 29; 606/96
See application file for complete search history.

(56) References Cited

U.S. PATENT DOCUMENTS

| | | | | |
|---|---|---|---|---|
| 4,941,826 A | * | 7/1990 | Loran et al. | 433/51 |
| 5,641,287 A | * | 6/1997 | Gittleman | 433/75 |
| 6,319,006 B1 | | 11/2001 | Scherer et al. | |
| 7,086,860 B2 | * | 8/2006 | Schuman et al. | 433/75 |
| 7,104,996 B2 | * | 9/2006 | Bonutti | 606/86 R |
| 7,146,739 B2 | * | 12/2006 | Ku et al. | 33/286 |

FOREIGN PATENT DOCUMENTS

| | | |
|---|---|---|
| JP | 63-315045 | 12/1988 |
| JP | 2001-170080 | 6/2001 |
| JP | 2003-260064 | 9/2003 |
| JP | 2006-101981 | 4/2006 |
| JP | 2006-271986 | 10/2006 |

OTHER PUBLICATIONS

U.S. Application No. 12/992,670 to Akira Takebayashi, which was filed on Nov. 15, 2010.

* cited by examiner

*Primary Examiner* — Cris L Rodriguez
*Assistant Examiner* — Matthew Seward
(74) *Attorney, Agent, or Firm* — Greenblum & Bernstein P.L.C.

(57) ABSTRACT

Provided is a surgical guide that enables a dentist to visually identify the tip of a drill during dental implant treatment, and does not allow the drill to tilt more than necessary, and enables sufficient cooling water to be provided so as not to cause bone burns, and is compatible with several different types of drills having different diameters. A first wire is embedded in a mockup in a same orientation as the orientation of a fixture of an implant is to be embedded. A guide member of a surgical guide is fitted to a tooth portion of the mockup. An adjusting mechanism adjusts such that an intersection line made by plane-shaped red laser light beam and green laser light beam from line laser modules is located on the first wire. The guide member is removed from the tooth portion of the mockup, and fitted to a tooth portion in the mouth, and the orientation of a drill is aligned with the intersection line. Drilling operation is performed in the aligned condition.

6 Claims, 6 Drawing Sheets

SURGICAL GUIDE AND A METHOD FOR POSITIONING A DRILL USING THE SURGICAL GUIDE

TECHNICAL FIELD

The present invention relates to a surgical guide used for three-dimensionally guiding the position and orientation of a drill when a guide hole, into which a dental implant fixture is to be embedded, is drilled in an alveolar bone of a patient.

BACKGROUND

A dental implant (hereinafter simply referred to "implant") used for implant treatment is made up of a fixture (implant body, for example, made of titanium) to be embedded into an alveolar bone at which a tooth is missing, an abutment coupled to and supporting the fixture, and a superstructure (artificial tooth crown) attached to the abutment. In the implant treatment that uses this type of implant, it is very important to accurately drilling a guide hole, into which the fixture is to be embedded, in the alveolar bone (see JP-A-2001-170080, for example).

Implant treatment can be categorized into two types: prosthetically oriented treatment (top-down treatment) and exist-bone orientated treatment. In the former, top-down treatment, a mockup (full-scale plaster model) of a tooth and an alveolar ridge of a patient is created. The mockup is mounted to an articulator in order to determine the geometries and position of a functionally and aesthetically optimized prosthesis (superstructure). Based on the determination, the position at which the fixture is to be embedded is decided. In the latter, exist-bone orientated treatment, a surgically and anatomically optimal position at which the fixture is to be embedded is determined based on the condition of the alveolar bone (the width, thickness, and density of the alveolar bone, the course of the nerve, or other factors) of a patient.

Currently, CT-based simulation software may be used for determining a prosthetically (functionally and aesthetically) desirable position, at which the fixture is to be embedded, in consideration of the condition or other factors of the alveolar bone of the patient. In addition, a stent that contains a contrast medium may be used in CT scanning in order to display onto the mockup the position, at which the fixture is to be embedded and which is determined on a CT display.

When a guide hole into which a fixture is to be embedded is drilled in an alveolar bone of a patient, three-dimensional positioning and orientation of the drill in the mouth of the patient are required. However, it is quite difficult to accurately drill a guide hole by freehand at the position the fixture should be embedded by looking at the CT display or the mockup. Therefore, various jigs, i.e., surgical guides, have been devised.

A typical example is a surgical guide that has a metallic guide ring for guiding a drill to the position at which the fixture is to be embedded. When a drill is placed into a hole in the guide ring and inserted along the hole in the guide ring, the drill is guided such that a guide hole is formed at the position the fixture should be embedded.

SUMMARY

However, the surgical guides having a guide ring as described above have problems as follows.
(1) The surgical guide covers the surgical site, and a dentist cannot visually identify the portion of the alveolar bone the tip of the drill is cutting, and thus the dentist may feel uneasy.
(2) A slight gap (free space) is required between the drill and the hole in the guide ring. However, the gap (free space) may allow the drill to tilt more than necessary because the thickness of the guide ring is thinner than the length of the drill. As a result, a hole having an inaccurate orientation may be formed.
(3) The alveolar bone in which the hole is to be formed is covered with the guide ring and periphery portions thereof, and the hole in the guide ring is blocked by the drill. As a result, a closed space is formed around the alveolar bone. Therefore, it is difficult to provide sufficient cooling water to the alveolar bone to be cut, which may cause bone burns.
(4) In order to form the guide hole into which the fixture is to be embedded, various types of drills are used. At first, a pilot drill having a small diameter is used, and then drills, each having a slightly larger diameter than the diameter of the drill used in the preceding drilling, are used. As a result, several types of surgical guides, each of which corresponds to each drill, are required, which increases cost.

Therefore, an aim of the present invention is to provide a surgical guide which enables a dentist to visually identify the tip of the drill, and which will not allow the drill to tilt more than necessary, and which enables sufficient cooling water to be provided and thus will not easily cause bone burns, and which is compatible with several types of drills having different diameters.

Means to Solve the Problems

The invention according to claim 1 relates to a surgical guide for three-dimensionally positioning a drill when a guide hole, into which a dental implant fixture is to be embedded, is drilled in an alveolar bone in the mouth. The surgical guide according to the invention includes an optical irradiation apparatus having at least two optical irradiating portions each for irradiating a plane-shaped light beam from a direction different from each other toward a wire, the wire being disposed in a mockup that imitates inside of the mouth of a patient and the wire being embedded corresponding to the position of the drill when the hole is formed; an adjusting mechanism for supporting the two optical irradiating portions movably forward, backward, rightward, leftward, upward, or downward and rotatably; and a detachably attachable guide member for supporting the adjusting mechanism, the guide member performing the positioning of the adjusting mechanism when the guide member is fitted to a tooth portion of the mockup and to an actual tooth portion of the patient that corresponds to the tooth portion the mockup. The surgical guide is characterized in that the guide member is fitted to the tooth portion of the mockup, and the adjusting mechanism adjusts the optical irradiating portions such that the two plane-shaped light beams linearly intersect on the wire, and the guide member is removed from the mockup and fitted to the actual tooth portion of the patient, and a hole is formed by the drill in a condition where the drill is aligned with the position at which the two plane-shaped light beams linearly intersect.

The invention according to claim 2 is characterized in that the light beams irradiated from the two optical irradiating portions in the surgical guide according to claim 1 have different colors.

The invention according to claim 3 is characterized in that the optical irradiation apparatus in the surgical guide according to claim 1 includes the optical irradiating portion adjustably supported by the adjusting mechanism, a light emitting portion for emitting light, and an optical fiber for coupling the optical irradiating portion and the light emitting portion.

The invention according to claim 4 relates to a method for positioning a drill, the method using an optical irradiation apparatus having two optical irradiating portions each for irradiating a plane-shaped light beam; an adjusting mechanism for adjusting the optical irradiating portions in order to adjust the position to be irradiated by the light beams that are irradiated from the optical irradiating portions; and a detachably attachable guide member for supporting the adjusting mechanism, and to be fitted to a tooth portion of a mockup that imitates inside of the mouth of a patient and to an actual tooth portion of the patient that corresponds to the tooth portion of the mockup. The method for positioning a drill according to the invention includes a first fitting step for fitting the guide member, together with the two optical irradiating portions and the adjusting mechanism, to the tooth portion of the mockup; an adjusting step for adjusting the adjusting mechanism such that an intersection line made by the plane-shaped light beams irradiated from the two optical irradiating portions is located on a wire that is embedded in the mockup corresponding to the position of the drill when a hole is formed; a removing step for removing the guide member, together with the two optical irradiating portions and the adjusting mechanism, from the tooth portion of the mockup; a second fitting step for fitting the removed guide member, together with the two optical irradiating portions and the adjusting mechanism, to the tooth portion of the patient; and a positioning step for positioning the drill such that the drill is located on the intersection line made by the two plane-shaped light beams.

The invention according to claim 5 is characterized in that two lines formed on the mockup by the plane-shaped light beams each irradiated from the two optical irradiating portions intersect each other and form an intersection point on the mockup, in the adjusting step in the method for positioning a drill according to claim 4.

The invention according to claim 6 is characterized in that the method for positioning a drill according to claim 4 includes a guide hole positioning step before the second fitting step. In the guide hole positioning step, a guide hole positioning jig is used for determining the position of the guide hole in the mouth of the patient. The guide hole positioning jig, on which the position of a base end portion of the wire embedded in the mockup is copied, is detachably attachable to the tooth portion of the mockup and to the tooth portion of the patient.

Effect of the Invention

According to the invention of claim 1, the guide member is fitted to the tooth portion of the mockup, and the adjusting mechanism adjust the two optical irradiating portions such that the two plane-shaped light beams intersect on the axis of the wire that is embedded in the mockup and that indicates the position at which the fixture is to be embedded. In other words, the intersection line made by the intersecting two plane-shaped light beams can be overlaid on (aligned with) the axis of the wire. That is, the position and orientation of the wire to be embedded can be specified by the intersection line of the light beams. Keeping the adjusted positioning, the guide member is removed from the tooth portion of the mockup, and fitted to the tooth portion of the patient. At this moment, the intersection line of the light beams indicates the position and orientation of the wire to be embedded, i.e., the position at which the fixture is to be embedded. Therefore, the guide hole can be formed accurately at the position the fixture is to be embedded, if drilling operation is performed while the axis of the drill is aligned with the intersection line of the light beams. In addition, a dentist can see the surgical site, and can cut the alveolar bone while visually identifying the tip of the drill. Moreover, the dentist can cut the alveolar bone while visually identifying that the drill does not tilt more than necessary; in other words, the axis of the drill does not deviate from the intersection line of the light beams. In addition, cooling water can be sufficiently provided, which is less likely to cause bone burns. Furthermore, a same surgical guide can be used for drills having different diameters. This saves cost for additional surgical guides otherwise required.

According to the invention of claim 2, the color of the two light beams differs from each other, and thus the two colors of the intersecting two plane-shaped light beams blend to make another color on the intersection line. Therefore, it is easy to visually identify the intersection line. If a light beam having a narrower line width is used, the two lines that irradiate the drill will become two lines having different colors and being parallel to and being close to each other. This further eases visual identification of the intersection line. In addition, if the surface of the drill is low-reflection treated, it will become easier to visually identify the intersection line.

According to the invention of claim 3, the optical irradiation apparatus includes the optical irradiating portion to be mounted in the mouth and the light emitting portion, which are discretely formed and coupled each other with the optical fiber. Therefore, the size of the portion of the optical irradiation apparatus to be mounted in the mouth can be significantly minimized. This reduces the burden of the patient, who otherwise needs to widely open the mouth during the treatment.

According to the invention of claim 4, the guide hole into which the fixture is to be embedded can be accurately formed at the position the fixture should be embedded, by the first fitting step, the adjusting step, the removing step, the second fitting step, and the positioning step.

According to the invention of claim 5, the intersection point drawn on the mockup by the two plane-shaped light beams corresponds to the position of the guide hole to be formed by the drill when the intersection point is reproduced on the mucosa in the mouth of the patient. Therefore, the position of the guide hole can be specified without using a special jig or the like.

According to the invention of claim 6, the position of the guide hole can be accurately determined by the guide hole positioning jig, for example, in a case where the positioning of the guide hole cannot be determined, or it is difficult to be determined, by the two plane-shaped light beams.

DETAILED DESCRIPTION OF THE PREFERRED EMBODIMENTS

Preferred embodiments of the present invention will be now described in detail, referring to the accompanying drawings. Same references are used throughout the drawings to designate like or equivalent configuration, and duplicated description thereof is omitted as appropriate. In addition, components that are not essential for explanation are omitted in the drawings as appropriate.

Embodiment 1

Figure 1:
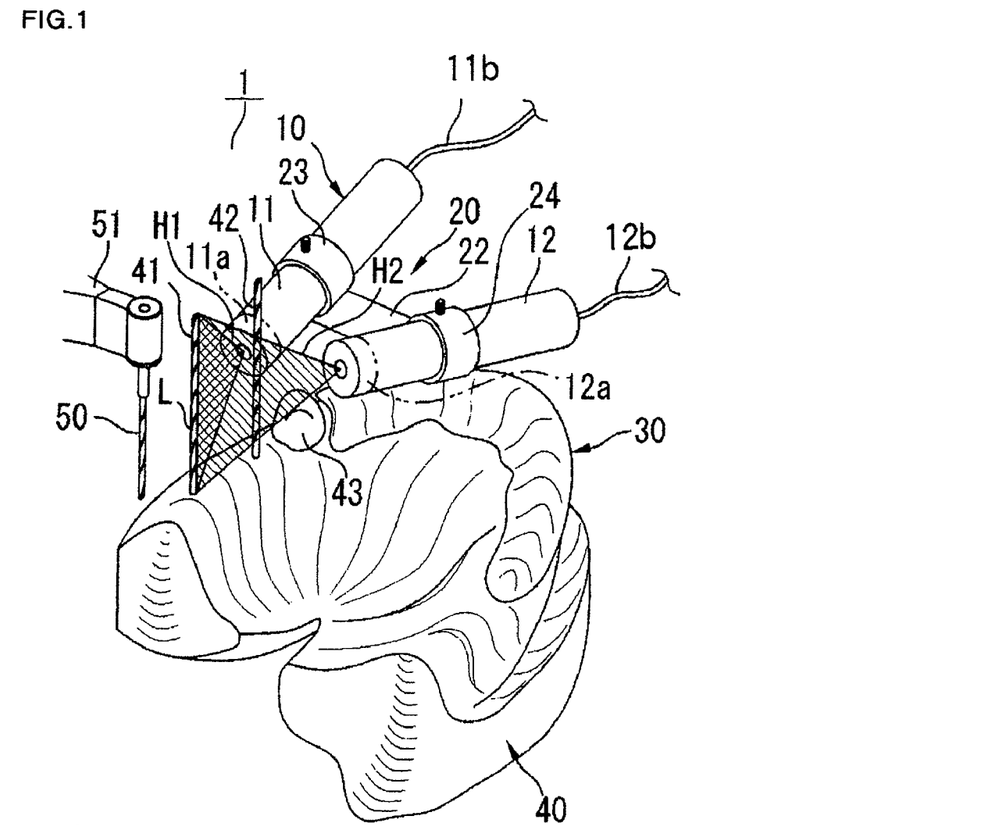
FIG. 1 is a perspective view illustrating a surgical guide 1 mounted to a mockup (plaster model) 40 into which a first wire 41 and a second wire 42 are embedded at the position the fixture is to be embedded.
Figure 2:
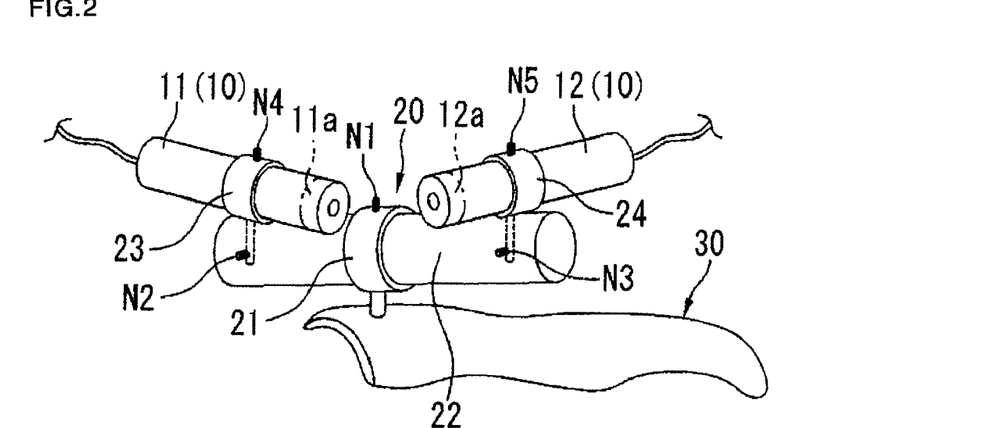
FIG. 2 illustrates an adjusting mechanism 20 of the surgical guide 1.
Figure 3:
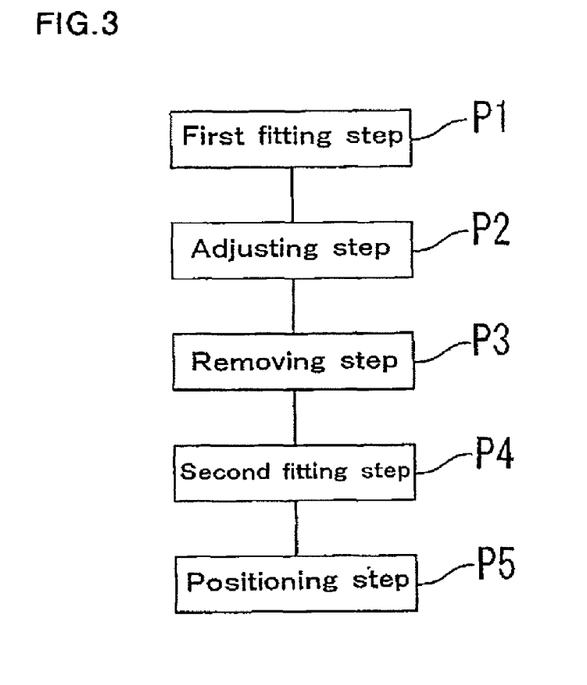
FIG. 3 illustrates steps of a method for positioning a drill 50.
Figure 4:
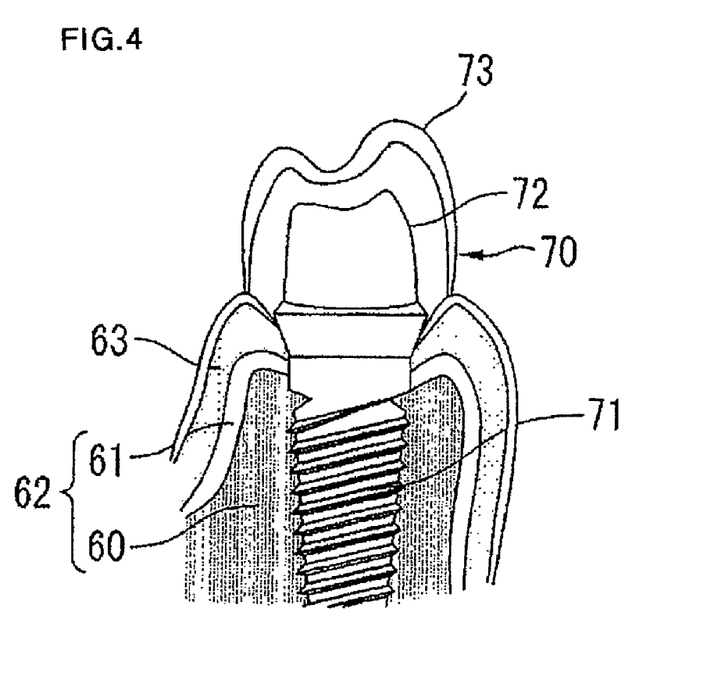
FIG. 4 illustrates an implant 70.

Referring to FIGS. 1 to 4, a surgical guide and a method for positioning a drill according to the present invention will be described. FIG. 1 is a perspective view that illustrates a surgical guide 1 mounted to a mockup (plaster model) 40 into which two wires, a first wire 41 and a second wire 42, are embedded. In FIG. 1, the mockup 40 is disposed upside down, and the first wire 41 and the second wire 42 are embedded in the mockup 40 at a portion teeth at right upper back are missing. FIG. 2 illustrates an adjusting mechanism 20 of the surgical guide 1. FIG. 3 illustrates steps of a method for positioning a drill 50. FIG. 4 illustrates an implant 70. Illustrated in the description hereinafter is an example in which implant treatment is performed at the portion in which two teeth right upper back of a patient are missing.

As shown in FIG. 1, the surgical guide 1 includes a laser apparatus (optical irradiation apparatus) 10, the adjusting mechanism 20, and a guide member 30. The entire surgical guide 1 is detachably attachable to the mockup 40 through the guide member 30, and also detachably attachable to inside of the mouth (having a same shape as the mockup 40, but not shown) of the patient.

Referring to FIG. 4, the implant 70 will be described. As shown in FIG. 4, a bone 62 composed of a soft cancellous bone 60 and a hard cortex bone 61, and a mucosa 63 that covers the bone remain at the portion the teeth (not shown) are missing. The implant 70 includes a fixture 71 embedded into a guide hole that is formed by drilling into the bone 62, an abutment 72 coupled to the fixture 71 and serving as a support, and a superstructure (artificial tooth crown) 73 attached to the abutment 72.

As shown in FIG. 1, the mockup 40 is a full-scale plaster model of maxillary teeth and an alveolar ridge made by impression (molding) of the inside of the mouth of the patient. In FIG. 1, the guide member 30 of the surgical guide 1 described later is fitted to (or covers) all other teeth except one tooth 43 at right back. The first wire 41 and the second wire 42 are embedded in the mockup 40 at a portion at right upper back, at which the teeth are missing and to which implant treatment is to be performed. The position and orientation at which the first wire 41 and the second wire 42 are to be embedded are determined as described later.

The relative positioning between the position, at which the fixture 71 is to be embedded (see FIG. 4) and which is determined by CT-based simulation software, and the position of a CT-scan stent that contains a contrast medium is measured on a CT display. Based on the measurement, a plurality of marks that indicate the position at which the fixture 71 is to be embedded are marked onto the CT-scan stent that contains the contrast medium. The stent is mounted to the mockup 40. A hole having a diameter of about 1 mm and a depth of about 10 mm is formed in the mockup 40 using the plurality of marks as a guide. The first wire (or the second wire 42) is embedded in the hole. As such, the position, at which the fixture 71 is to be embedded and which is determined by the simulation, can be displayed as the position and orientation of the first wire 41 (or the second wire 42) embedded on the mockup 40. In other words, the guide hole into which the fixture 71 is to be mounted should be formed in the mouth of the patient at a same position and orientation as the position and orientation of the first wire 41 (or the second wire 42) is embedded at.

As shown in FIG. 1, the surgical guide 1 includes the laser apparatus 10 as an optical irradiation apparatus, the adjusting mechanism (supporting member) 20, and the guide member 30. The laser apparatus 10 includes two line laser modules 11 and 12, and a power source (not shown) coupled to the modules 11 and 12 via lead wires 11b and 12b. Each of the line laser modules 11 and 12 includes a laser emitting portion (light emitting portion), and a laser irradiating portion (optical irradiating portion) 11a or 12a having a collimator lens and a line generator, and emits a plane-shaped laser light beam H1 or H2. In FIG. 1, the laser light beam H1 is shown as a rectangular shaded with slants upward to the right, and the laser light beam H2 is shown as a rectangular shaded with slants downward to the right. For example, when the laser light beams H1 and H2 are irradiated to a flat surface, the light beams draw lines on the flat surface. In this embodiment, for example, the line laser module 11 emits a red laser light beam H1, and the line laser module 12 emits a green laser light beam H2. Examples of the optical irradiation apparatus other than the laser apparatus 10 described above include a line LED, for example.

As shown in FIG. 2, the adjusting mechanism 20 includes a first annular member 21 fixed to the guide member 30 described later; a rotatable, rod-shaped supporting member 22 supported by the first annular member 21; and second annular members 23 and 24 supported via a hole formed in a radial direction of the supporting member 22 and capable of being swung to the right and left. Each of the second annular members 23 and 24 supports the line laser module 11 or 12 described above, respectively. The orientation of the line laser modules 11 and 12 can be changed up or down by loosing a screw N1 of the adjusting mechanism 20 and rotating the supporting member 22. In addition, the orientation the line laser modules 11 and 12 can be changed to the right or left by loosing screws N2 and N3 and swinging the second annular members 23 and 24 to the right or left. Also, by loosing screws N4 and N5 and moving the line laser modules 11 and 12 along the center axis thereof (not shown), the plane-shaped laser light beams H1 and H2 can be moved in the direction of the center axis thereof. Furthermore, the plane-shaped laser light beams H1 and H2 can be rotated by rotating the line laser modules 11 and 12.

The adjusting mechanism 20 can adjust the orientation and rotation of the line laser module 11 such that a plane made by the laser light beam H1 is overlaid on the axis of the first wire 41 (or the second wire 42). At this moment, a red line is drawn on the axis of the first wire 41 (or the second wire 42). Similarly, the adjusting mechanism 20 can adjust the orientation and rotation of the line laser module 12 such that a plane made by the laser light beam H2 is overlaid on the axis of the first wire 41 (or the second wire 42). At this moment, a green line is drawn on the axis of the first wire 41 (or the second wire 42).

The laser irradiating portions 11a and 12a at tip portions of the line laser modules 11 and 12 described above may be formed rotatably such that the laser light beams H1 and H2 may be rotated by rotating the portions 11a and 12a. In this case, for example, the positioning of the line laser modules 11 and 12 is performed by loosing the screws N4 and N5 and moving the modules in a direction of the center axis thereof, and then the laser light beams H1 and H2 can be rotated by rotating the laser irradiating portions 11a and 12a at the tip portion after tightening the screws N4 and N5. If it is not necessary to move the line laser modules 11 and 12 in the direction of the center axis, for example, the laser light beams H1 and H2 can be rotated simply by rotating only the laser irradiating portions 11a and 12a at the tip portion, without the need of loosing the screws N4 and N5.

In the example of FIG. 1, the planes made by the red and green laser light beams H1 and H2 intersect on the axis of the first wire 41. In other words, an intersection line L made by the plane-shaped red laser light beam H1 and the plane-shaped green laser light beam H2 that intersect each other is located (overlaid) on the axis of the first wire 41. In this case, the two colors, red and green, blend to make yellow on the intersection line L.

Effective approaches in a method for efficiently adjusting the adjusting mechanism 20 are to adjust the adjusting mechanism 20 while only one of the line laser modules is lit up, and to attach a piece of paper of about 10 mm×20 mm onto the wire and roughly adjust the adjusting mechanism 20 while the paper is irradiated by the laser light beam and a line is drawn on the paper.

Figure 5A:
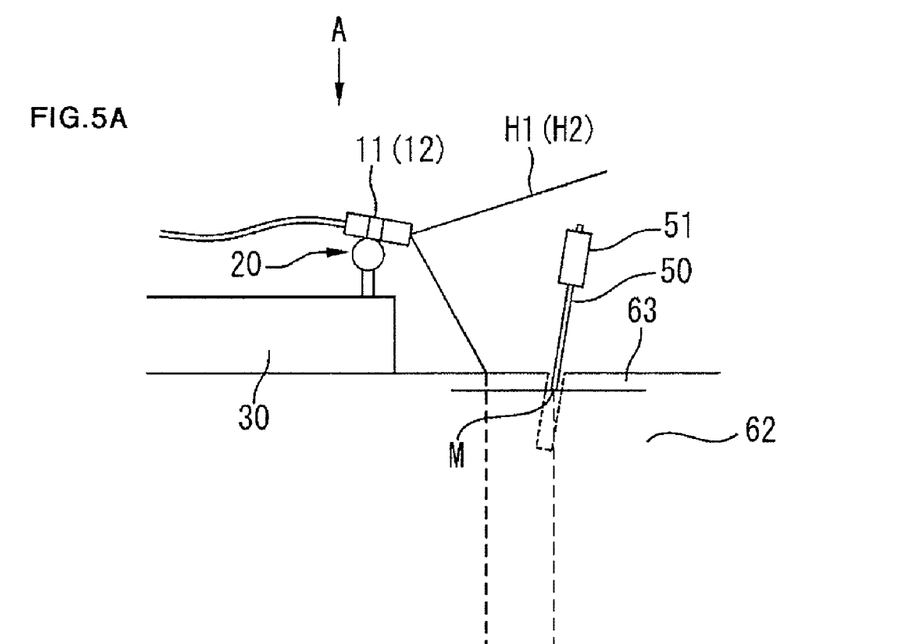
FIG. 5A illustrates a positioning step P5.
Figure 5B:
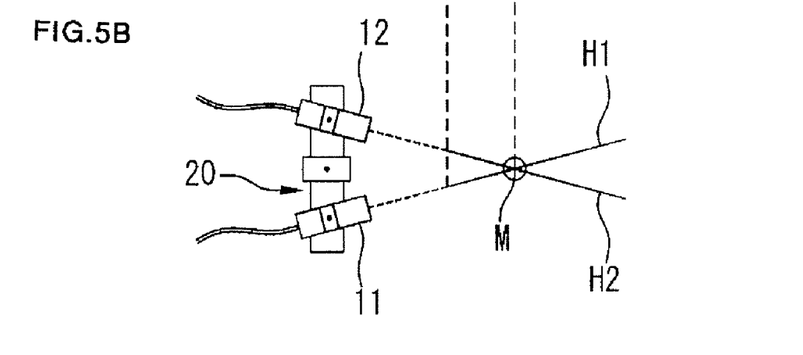
FIG. 5B is a view observed from A direction in FIG. 5A.

In the example described above, each of the laser light beams H1 and H2 irradiates the first wire 41 from the lower end to upper end of the wire. In other words, the lower ends of the laser light beams H1 and H2 on a flat surface coincide with the lower end of the first wire 41, and the upper ends thereof coincide with the upper end of the first wire 41. However, the present invention is not limited to the example. For example, the laser light beams H1 and H2 may irradiate a range within the length of the first wire 41; in other words, from a portion upper than the lower end to a portion lower than the upper end. Alternatively, the laser light beams H1 and H2 may irradiate beyond the length of the first wire 41. Especially in a case where the laser light beams H1 and H2 irradiate beyond the lower end of the first wire 41; in other words, the line laser modules 11 and 12 are directed slightly downward such that the laser light beams H1 and H2 irradiate the mockup 40 from a point nearer than the lower end of the first wire 41, the line drawn on the surface the mockup 40 by one laser light beam H1 and the line drawn on the mockup 40 by the other laser light beam H2 intersect each other and forms an intersection point on the surface of the mockup 40. As shown in FIGS. 5A and 5B, the intersection point indicates the position of the guide hole into which the fixture 71 is to be embedded (the position that corresponds to the mark M in FIGS. 5A and 5B) on the mucosa in the mouth when the guide portion 30 of the surgical guide 1 is removed from the mockup 40 and mounted (fitted) to a tooth portion of the patient. In other words, the position of the guide hole can be specified without using a special jig or the like.

As such, the positioning of the guide hole in the mouth can be easily performed as described above, by the adjustment in an adjusting step P2 described later such that the two lines formed on the mockup 40 by the plane-shaped light beams each irradiated from the two line laser modules 11 and 12 intersect each other and form an intersection point on the mockup 40.

Regarding the adjusting mechanism, another adjusting mechanism 20A will be described later referring to FIG. 8.

The guide member 30 is made of, for example, resin or polycarbonate and formed such that it fits with the tooth portion of the mockup 40 that corresponds to a remaining tooth portion of the patient. The guide member 30 supports the adjusting mechanism 20 described above. The guide member 30 is detachably attachable to the tooth portion of the mockup 40, and makes the tooth portion of the mockup 40 serve as a fixed base of the adjusting mechanism 20 as well as of the line laser modules 11 and 12, when the guide member 30 is mounted and fitted to the mockup 40. The guide member 30 is detachably attachable also to the remaining tooth portion of the patient, and makes the remaining tooth portion of the patient serve as a fixed base of the adjusting mechanism 20 as well as of the line laser modules 11 and 12, when the guide member 30 is mounted and fitted to the remaining tooth portion.

The surgical guide 1 having a configuration as described above performs positioning of the drill 50 in the steps shown in FIG. 3.

(First Fitting Step P1)

As shown in FIG. 1, the guide member 30 of the surgical guide 1 is fitted to the tooth portion of the mockup 40 so that the entire surgical guide 1 is mounted to the mockup 40.

(Adjusting Step P2)

At first, only the line laser module 11 is lit up and a red plane-shaped laser light beam H1 is emitted. The adjusting mechanism 20 adjusts the orientation and rotation of the line laser module 11 such that a red line made by the laser light beam H1 is drawn on the axis of the first wire 41. Similarly, only the line laser module 12 is lit up and a green line made by the laser light beam H2 is drawn on the axis of the first wire 41. Then, both of the line laser modules 11 and 12 are simultaneously lit up, which makes the red and green laser light beams H1 and H2 be overlaid on each other and create a yellow line (intersection line L) on the axis of the first wire 41.

In this case, as shown in FIG. 1, the orientation and rotation of the line laser modules 11 and 12 may be adjusted such that the lower ends of the two colors of laser light beams H1 and H2 coincide with (intersect at) the lower end of the first wire 41, and form an intersection point. As shown in FIGS. 5A and 5B, the intersection point indicates the position (corresponding to the position of the mark M in FIGS. 5A and 5B) of the guide hole into which the fixture 71 is to be embedded on the mucosa in the mouth when the guide portion 30 of the surgical guide 1 is removed from the mockup 40, and mounted (fitted) to the tooth portion of the patient, in steps described later.

In addition, if the orientation of the tip portions (portions from which the laser light beams H1 and H2 are irradiated) of each of the line laser modules 11 and 12 is slightly lowered from the condition described above in which the lower ends of the two laser light beams H1 and H2 intersect exactly at the lower end of the first wire 41, the lower ends of the laser light beams H1 and H2 will irradiate the surface of the mockup 40 linearly from a portion nearer than the lower end of the first wire 41. In this case, the intersection point of two lines drawn on the surface of the mockup 40 by the lower ends of the two laser light beams H1 and H2 coincides with the lower end of the first wire 41. Therefore, if the surgical guide 1, in which the adjusted positioning is kept, is mounted (fitted) to the tooth portion of the patient after it undergoes a subsequent removing step P3 and a second fitting step P4, the intersection point described above will be reproduced in the mouth of the patient as an intersection point of two lines drawn on the mucosa 63 by the lower ends of the two laser light beams H1 and H2, as shown in FIGS. 5A and 5B. The intersection point indicates the position of a guide hole into which the fixture 71 is to be embedded (the position corresponds to the position of the mark M in FIGS. 5A and 5B). In other words, the position of a guide hole can be visually identified as the intersection point of the two lines, and thus the visual identification of the point is easy and the position of the guide hole can be accurately identified.

(Removing Step P3)

The fitting of the guide member 30 to the tooth portion of the mockup 40 is released so that the entire surgical guide 1 is removed from the mockup 40.

(Second Fitting Step P4)

The guide member 30 is fitted to the remaining tooth portion in the mouth of the patient so that the entire surgical guide 1 is mounted in the mouth.

(Positioning Step P5)

A mark is marked at the intersection point made by the two laser light beams H1 and H2 on the surface of the mucosa such that the mark reaches the surface of the bone, by using an electrosurgical knife (not shown) or the like. The mucosa 63 (see FIG. 4) at the marked portion is removed by punching or flapping. After that, at the position of the mark on the surface of the bone, an indentation mark M is marked using a marking bar (not shown). (In a flapping approach, the indentation mark M may be marked using a marking bar at the intersection point made by the two laser light beams H1 and H2 on the surface of the bone after the flapping.) After that, the orientation of a contra head 51 is adjusted such that the tip of a drill (pilot drill) 50 mounted to the contra head 51 is aligned with the mark M, and such that a yellow line made by the overlaying red and green laser light beams H1 and H2 is drawn on the axis of the drill 50; that is, the intersection line L made by the two laser light beams H1 and H2 is located (overlaid) on the axis of the drill 50. (This adjustment may become easier if a piece of paper of about 10 mm×20 mm is previously pasted onto the contra head 51.) Keeping the adjusted condition, drilling operation is started. At this moment, the axis of the drill 50 can be moved along the intersection line L. The guide hole into which the fixture 71 is to be embedded is gradually expanded by using drills each having a slightly larger diameter than the diameter of the drill used in the preceding drilling.

In FIG. 1, each of the lower ends of the two laser light beams H1 and H2 impinges on the surface of the mockup 40 at a same position. However, alternatively, two lines that intersect each other may be drawn on the surface of the mucosa by tilting the orientation of the line laser modules 11 and 12 slightly downward. This makes it easier to visually identify the position at which the two laser light beams H1 and H2 intersect on the mucosa surface (see FIG. 5).

Figure 6A:
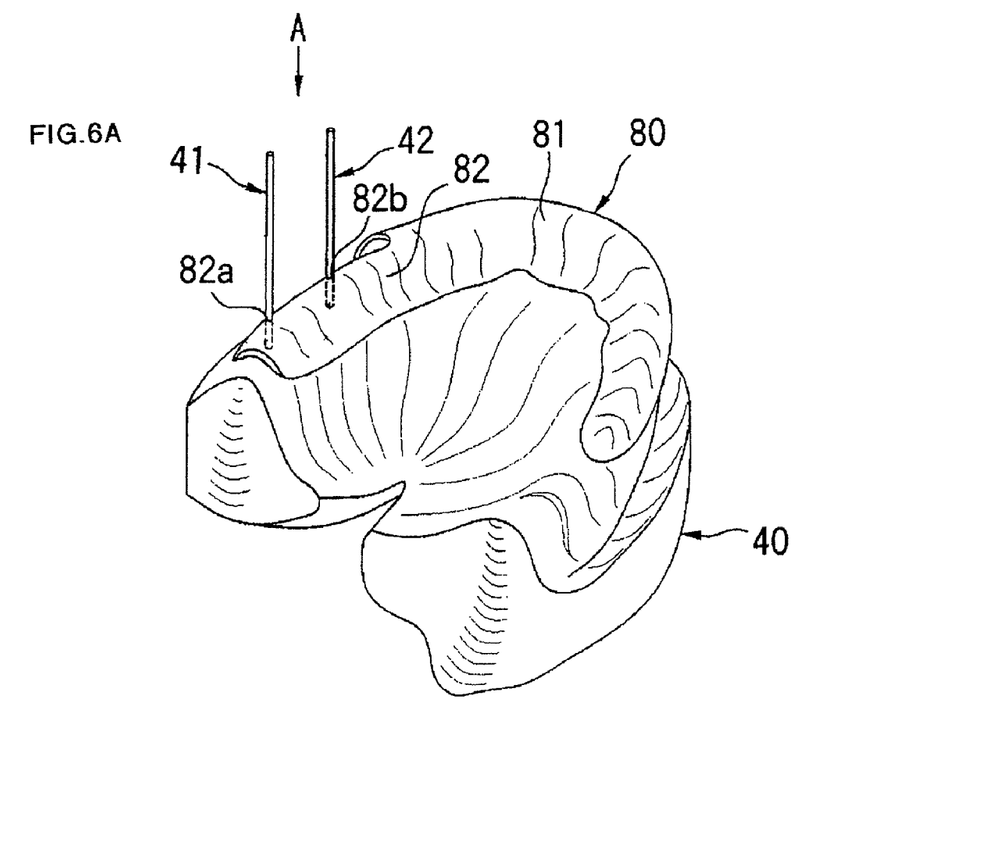
FIG. 6A illustrates a surgical guide 80.
Figure 6B:
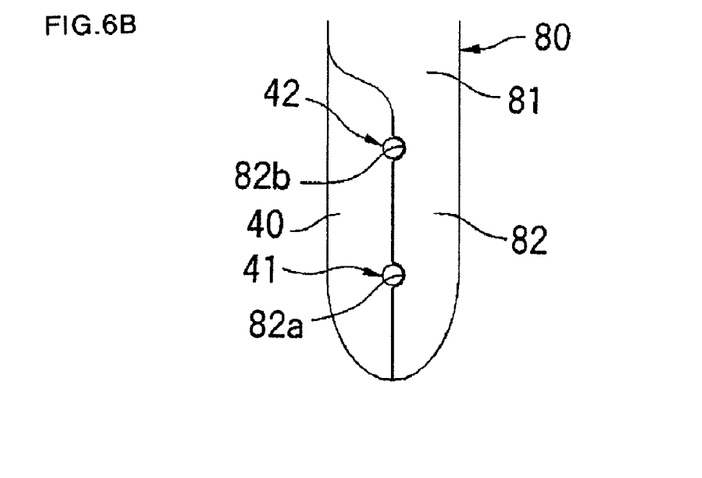
FIG. 6B is a view observed from A direction in FIG. 6A.

In the example described above, the position of the mark M is determined by the intersection point made by the two laser light beams H1 and H2 on the surface of the mucosa. However, if it is difficult to visually identify the position of the intersection point on the surface of the mucosa depending on use environment or other factors, a surgical guide (guide hole positioning jig) 80 as shown in FIGS. 6A and 6B may be used as a jig for determining the position of the mark M. In this case, before the second fitting step P4 described above, a guide hole positioning step is provided. The surgical guide (guide hole positioning jig) 80 is detachably attachable to the tooth portion of the mockup 40 and to the tooth portion of the patient, in the guide hole positioning step. On the surgical guide, the positions of base end portions of the wires 41 and 42 embedded in the mockup 40 are copied, and the surgical guide is used for determining the position of the guide hole in the mouth of the patient. More specifically, as shown in FIGS. 6A and 6B, the surgical guide 80 includes a guide member 81 and a wire guide 82, which are made of resin or polycarbonate and formed integrally such that the surgical guide 80 fits to the tooth portion of the mockup 40 and to the wires 41 and 42. As shown in FIG. 6B, the wire guide 82 is formed such that half (left half in FIG. 6B) on cheek side from the wires 41 and 42 is cut out, and the portions that correspond to the wires 41 and 42 form half circular base end guides 82a and 82b. The guide member 81 is mounted and fitted to the remaining tooth portion of the patient, and a mark is marked on the surface of the mucosa at portions the base end guides 82a and 82b are located such that the mark reaches the surface of the bone, by using an electrosurgical knife (not shown) or the like. The mucosa 63 at the marked portion is removed by punching or flapping. After that, the position of the mark on the surface of the bone is marked with an indentation mark M by using a marking bar (not shown). As such, the mark M at the tip of the drill 50 is determined, which is used when a guide hole into which the fixture 71 is to be embedded is formed by the drill 50.

When the fixture 71 is embedded in the guide hole formed as described above, the position of the fixture 71 coincides with the position at which the fixture is to be embedded and which is determined by simulation software. This is because three dimensional positioning and orientation of the drill 50 in the mouth coincides with the position and orientation of the first wire 41 embedded on the mockup 40, as described above.

According to the embodiment described above, the following advantages can be obtained.

(1) A dentist can observe the surgical site. The dentist does not feel uneasy because he or she can perform drilling operation while visually identifying the portion of the alveolar bone the tip of the drill 50 is cutting.

(2) Moving the drill 50 along the intersection line L made by the two laser light beams H1 and H2 can prevent the drill 50 from tilting more than necessary.

(3) Sufficient cooling water can be supplied to the portion at which the hole is formed, which is less likely to cause burns.

(4) To form a guide hole into which the fixture 71 is to be embedded, various drills 50 having different diameters are generally used. At first, a drill (pilot drill) 50 having a small diameter is used, and then drills, each having a slightly larger diameter than the diameter of the drill used in the preceding drilling, are used. Nevertheless, a same surgical guide 1 can be used for the drills 50 each having a different diameter. This saves cost for additional surgical guides otherwise required.

Furthermore, additional advantages can be obtained as follows.

(5) The surgical guide can be applied to either of a flapping approach in which the mucosa is stripped so that the surface of the bone is widely exposed, or a flapless approach in which a hole, which is large enough to insert the fixture therein, is punched in the mucosa.

(6) In conventional technology, the guide ring contacts the drill, and thus the vibration of the drill causes the guide member to be easily detached or become unstable; however, the present embodiment is free from such disadvantages.

Visual identification of the laser light beams H1 and H2 that irradiate the surface of the drill 50 can be improved if a red laser light beam H1 and a green laser light beam H2, each having a narrower line width (for example, about 100 micrometers) than the diameter of the drill 50 (about 1.6 mm), are used and the surface of the drill 50 is low-reflection treated.

In the example described above, the red laser light beam H1 is emitted from one of the line laser module 11 in the laser apparatus 10, and the green laser light beam H2 is emitted from the other one line laser module 12. However, alternatively, both of the line laser modules 11 and 12 may emit green laser light beams H1 and H2. Depending on use environment, green laser light beams H1 and H2 may provide better visual identification than red laser light beams. In such a case, both of the laser light beams H1 and H2 may be green. Under an environment where a red laser light beam can provide sufficient visual identification, both of the laser light beams H1 and H2 may be red.

Embodiment 2

In the embodiment 1 described above, components of the laser apparatus 10 except the power source and the lead wires 11b and 12b are integrally configured. However, alternatively, only the laser irradiating portions 11a and 12a may be mounted to the adjusting mechanism 20, and other components may be coupled to the laser irradiating portions 11a and 12a through an optical fiber (not shown). In this case, the size of the portion of the laser apparatus to be mounted in the mouth can be made significantly small. This reduces the burden of the patient, who otherwise needs to widely open the mouth during the treatment.

Figure 7:
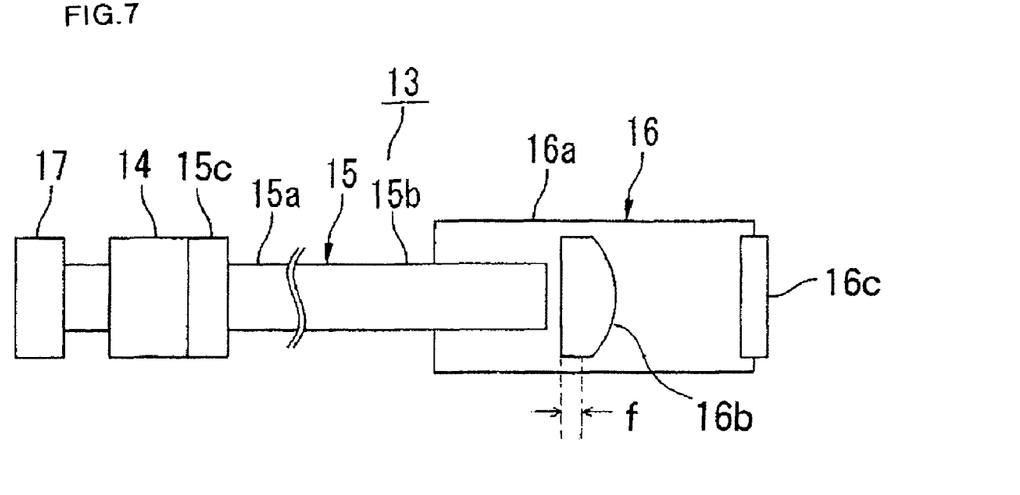
FIG. 7 schematically illustrates a laser apparatus 13 in which an optical fiber 15 is used.

FIG. 7 illustrates an example of a laser apparatus using such an optical fiber.

A laser apparatus 13 shown in FIG. 7 includes a laser light source 14 as a light emitting portion, an optical fiber 15, a base end portion 15a of the optical fiber 15 being coupled to the laser light source 14 through a coupler 15c, and a laser irradiating portion 16 disposed at a tip portion 15b of the optical fiber 15.

The laser light source 14 may be made of, for example, a semiconductor laser (red laser diode or green DPSS laser) and an APC (automatic power controller), and is coupled to a power source 17. The laser light source 14 may emit a laser light beam, for example, having a wavelength in a range of 532 nm (green) to 670 nm (red) and having an output of about 1 mW, through the coupler 15c toward the base end portion 15a of the optical fiber 15.

A single mode or multi mode fiber having an outer diameter of about 1 mm to 3 mm may be used for the optical fiber 15. The optical fiber 15 guides the light beam emitted from the laser light source 14 described above to the laser irradiating portion 16.

For the optical fiber used herein, a single mode fiber, which can provide a narrower line width, is more preferable than a multi mode fiber. (PM mode fiber may also be used.)

The laser irradiating portion 16 includes a pipe 16a that covers the tip portion 15b of the optical fiber 15, a collimator lens 16b retained by the pipe 16a, and a line generator 16c mounted at a tip of the pipe 16a.

The collimator lens 16b may be disposed, for example, such that it is located spaced from the tip of the optical fiber 15 by a focal length f. The collimator lens 16b makes the light beam emitted from the optical fiber 15 into cylindrical parallel light.

The line generator 16c may be made of a Powell lens or a cylindrical lens, and disposed in front of the collimator lens 16b and at the tip of the pipe 16a. The cylindrical parallel light that passed through the collimator lens 16b becomes a plane-shaped laser light beam H1 (or laser light beam H2) after it passes through the line generator 16c. The laser light beam H1 (or laser light beam H2) expands in a shape of a rectangular as shown in FIG. 1, and draws a line on the axis of the wire 41 (or wire 42) embedded onto the mockup 40 and on the mucosa of the mockup 40.

Figure 8A:
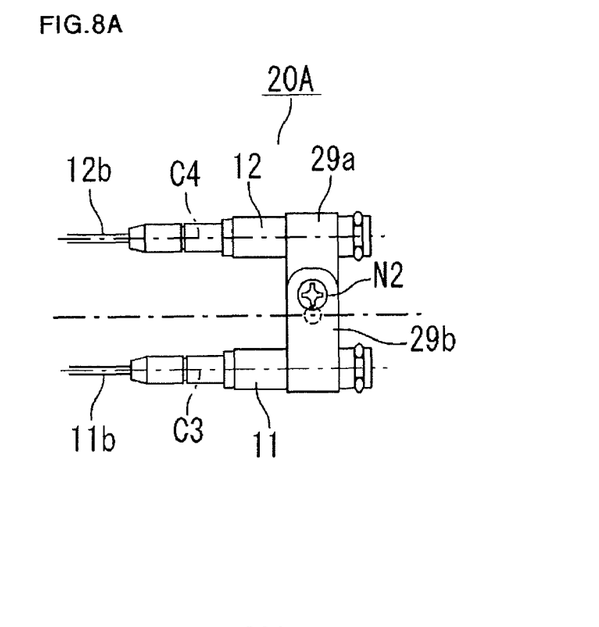
FIG. 8A is a top view of an adjusting mechanism 20A.
Figure 8B:
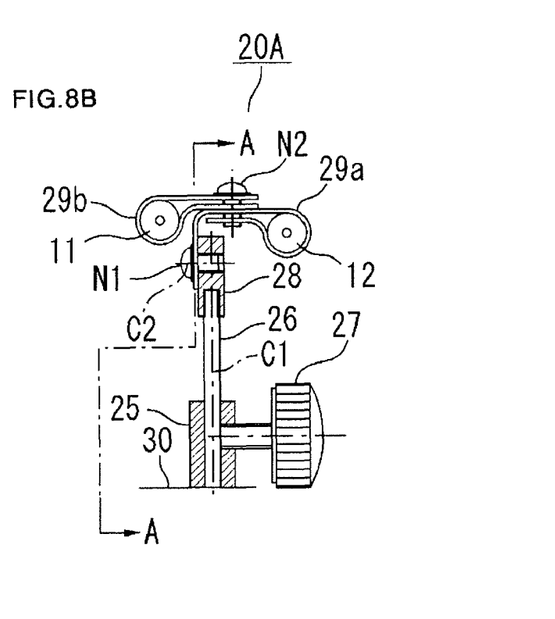
FIG. 8B is a view observed from right side in FIG. 8A.
Figure 8C:
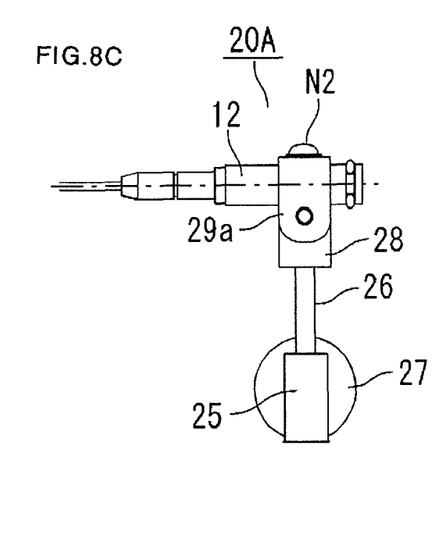
FIG. 8C is a view taken along line A-A in FIG. 8B.

Referring now to FIGS. 8A, 8B, and 8C, an adjusting mechanism 20A that differs from the adjusting mechanism 20 described above will be described. FIG. 8A illustrates a top view of the adjusting mechanism 20A. FIG. 8B is a view observed from right side of in FIG. 8A. FIG. 8C is a view taken along line A-A of FIG. 8B. As shown in FIG. 8B, the adjusting mechanism 20A includes a cylindrical shaft holder 25 embedded into the guide member 30 shown in the lower end of FIG. 8B. In the shaft holder 25, a shaft 26 is inserted from above. The lower end of the shaft 26 is fixed to the shaft holder 25 with a knurled screw 27. The shaft 26 can be moved up or down or rotated by loosing the knurled screw 27. At the upper end of the shaft 26, a block-like base member 28 is screwed. A female screw is threaded into the base member 28 in a horizontal direction in FIG. 8B. A male screw N1 is screwed to the female screw to fix a first holder 29a to the base member 28. The first holder 29a is a member for retaining the line laser module 12, and is formed by folding or bending a strip of a metal plate. More specifically, in FIG. 8B, the first holder 29a is formed such that a vertical portion fixed with the male screw N1 is vertically extended upward, and then bent at 90 degrees to the right, and extended horizontally, and bent circularly downward along the outer periphery of the line laser module 12, and then extended to the left. A second holder 29b that retains the line laser module 11 is formed in a shape substantially same as the first holder 29a except the vertical portion thereof. The second holder 29b is engaged with the first holder 29a by a male screw N2.

The adjusting mechanism 20A having a configuration described above can easily adjust the position of the line laser modules 11 and 12. The adjustment in height can be done by moving the shaft 26 up or down after loosing the knurled screw 27. The adjustment in a rotational direction with respect to the center axis C1 can be done by rotating the shaft 26 around the center axis C1 after loosing the knurled screw 27. The adjustment in a rotational direction with respect to the center axis C2, i.e. the swinging to up or down, can be done by loosing the male screw N1. Furthermore, a relative angle made by the center axes C3 and C4 of the line laser modules 11 and 12 in FIG. 8A can be adjusted by loosing the male screw N2. The line laser modules 11 and 12 are in parallel with each other in FIG. 8A. However, as shown in FIG. 1, the line laser modules 11 and 12 may irradiate, for example, the first wire 41 when disposed with their tip portions on one side (right side in FIG. 8A) being close each other and their tip portions on the other side being spaced apart.

The adjusting mechanism 20A described above can readily create a desired irradiation condition by the line laser modules 11 and 12 in a combination of the position adjustments as described above as appropriate.

1 surgical guide
10 laser apparatus (optical irradiation apparatus)
11a laser irradiating portion (optical irradiating portion)
12a laser irradiating portion (optical irradiating portion)
13 laser apparatus (optical irradiation apparatus) using an optical fiber
20 adjusting mechanism
30 guide member
40 mockup
50 drill
70 implant (dental implantation)
71 fixture
80 surgical guide (guide hole positioning jig: dedicatedly used for indicating the mark M)
H1 laser light beam
H2 laser light beam
L intersection line
M mark M
P1 first fitting step
P2 adjusting step
P3 removing step
P4 second fitting step
P5 positioning step

The invention claimed is:

1. A surgical guide used for performing three dimensional positioning of a drill when a guide hole into which a dental implant fixture is to be embedded is formed in an alveolar bone in the mouth by the drill, the surgical guide comprising:
   an optical irradiation apparatus having at least two optical irradiating portions each configured to irradiate a plane-shaped light beam from a direction different from each other and toward a position corresponding to a position in which a wire is embeddable in a mockup that imitates an inside of the mouth of a patient,
   an adjusting mechanism that supports the two optical irradiating portions movably forward, backward, rightward, leftward, upward, or downward, and rotatably, and
   a detachably attachable guide member that supports the adjusting mechanism and is configured to position the adjusting mechanism when the guide member is fitted to a tooth portion of the mockup or to an actual tooth portion of the patient that corresponds to the tooth portion of the mockup,
   wherein, when the guide member is fitted to the tooth portion of the mockup, the adjusting mechanism is configured to adjust the optical irradiating portions such that the two plane-shaped light beams linearly intersect at the position corresponding to the position in which the wire is embeddable in the mock up,
   wherein the guide member is configured to be removed from the mockup and fitted to the actual tooth portion of the patient, and
   wherein the guide member is configured to allow a hole to be formed by the drill while the drill is aligned with the position at which the two plane-shaped light beams linearly intersect.

2. The surgical guide according to claim 1, further comprising the colors of the light beams irradiated from the two optical irradiating portions being different from each other.

3. The surgical guide according to claim 1, the optical irradiation apparatus comprises an optical fiber that couples a light emitting portion to a corresponding one of the two optical irradiating portions.

4. A method for positioning a drill by using an optical irradiation apparatus that comprises two optical irradiating portions each for irradiating a plane-shaped light beam;
   providing an adjusting mechanism that adjusts the optical irradiating portions in order to adjust the position to be irradiated by the light beams irradiated from the optical irradiating portions; and
   providing a detachably attachable guide member that supports the adjusting mechanism, and wherein the guide member is to be fitted to a tooth portion of a mockup that imitates an inside of the mouth of a patient and to an actual tooth portion of the patient that corresponds to the tooth portion the mockup, the method comprising:
   fitting the guide member, together with the two optical irradiating portions and the adjusting mechanism, to the tooth portion of the mockup;
   adjusting the adjusting mechanism such that an intersection line made by the plane-shaped light beams irradiated from the two optical irradiating portions is located on a wire that is embedded in the mockup corresponding to the position of the drill when a hole is formed;
   removing the guide member, together with the two optical irradiating portions and the adjusting mechanism, from the tooth portion of the mockup;
   fitting the removed guide member, together with the two optical irradiating portions and the adjusting mechanism, to the tooth portion of the patient; and
   positioning the drill such that the drill is located on the intersection line made by the two plane-shaped light beams.

5. The method for positioning a drill according to claim 4, wherein the adjusting further comprises forming two lines on the surface of the mockup, by the plane-shaped light beams each irradiated from the two optical irradiating portions, that intersect each other and thereby form an intersection point on the mockup.

6. The method for positioning a drill according to claim 4, further comprising positioning a guide hole before the fitting of the removed guide member, wherein a guide hole positioning jig is used to determine the position of the guide hole in the mouth of the patient, and wherein the guide hole positioning jig is detachably attachable to the tooth portion of the mockup and to the tooth portion of the patient, and wherein the position of a base portion of the wire embedded in the mockup is copied on the guide hole positioning jig.

* * * * *